United States Patent [19]

Lee et al.

[11] 4,250,257
[45] Feb. 10, 1981

[54] WHOLE BLOOD ANALYSES IN POROUS MEDIA

[75] Inventors: Martin J. Lee, Leonia; Michael J. Malin, Park Ridge, both of N.J.

[73] Assignee: Technicon Instruments Corporation, Tarrytown, N.Y.

[21] Appl. No.: 936,436

[22] Filed: Aug. 24, 1978

[51] Int. Cl.³ .............. C12M 1/34; G01N 21/27; G01N 31/06; G01N 33/52

[52] U.S. Cl. ..................... 435/4; 23/230 R; 23/230 B; 422/56; 422/58; 422/66; 422/69; 435/291; 435/299; 435/805

[58] Field of Search ............. 23/230 B, 230 R; 422/56, 58, 66, 69; 195/103.5 R; 435/299–301, 805, 4, 25, 26, 291

[56] References Cited

U.S. PATENT DOCUMENTS

| | | | |
|---|---|---|---|
| 3,146,163 | 8/1964 | Brewer | 195/103.5 R |
| 3,368,872 | 2/1968 | Natelson | 422/66 |
| 3,453,180 | 7/1969 | Fraser, Jr. | 422/56 X |
| 3,526,480 | 9/1970 | Findl et al. | 422/66 |
| 3,585,004 | 6/1971 | Mast | 422/56 |
| 3,607,093 | 9/1971 | Stone | 435/299 X |
| 3,725,004 | 4/1973 | Johnson et al. | 23/230 B |
| 3,791,930 | 2/1974 | Saxholm | 195/103.5 R |
| 3,798,004 | 3/1974 | Zerachia et al. | 422/56 |
| 3,814,670 | 6/1974 | Freake et al. | 435/301 |
| 3,901,657 | 8/1975 | Lightfoot | 422/56 |
| 3,975,162 | 8/1976 | Renn | 422/56 X |
| 3,981,776 | 9/1976 | Saxholm | 422/69 X |
| 3,990,849 | 11/1976 | Lee et al. | 23/230 B |

FOREIGN PATENT DOCUMENTS

| | | | |
|---|---|---|---|
| 2152099 | 5/1973 | Fed. Rep. of Germany | 422/56 |
| 2416047 | 10/1975 | Fed. Rep. of Germany | 422/56 |

*Primary Examiner*—Arnold Turk
*Attorney, Agent, or Firm*—S. P. Tedesco

[57] ABSTRACT

Method and apparatus for analyzing whole blood samples which feature impregnating a gel medium used for the analysis of the whole blood sample with an inert substance. When the whole blood sample is placed on the gel medium, the inert substance diffuses from the gel as the plasma solutes of the blood diffuse into the gel. The amount of the inert substance diffusing from the gel medium is inversely proportional to the hematocrit of the blood sample. In one embodiment, plasma solutes are caused to react with one or more reagents in the gel medium to assay various specific analytes. Also, the hematocrit, indicated by the diffusion rate of the inert substance from the gel, is determined and used to correct such assay.

38 Claims, 14 Drawing Figures

FIG. 1
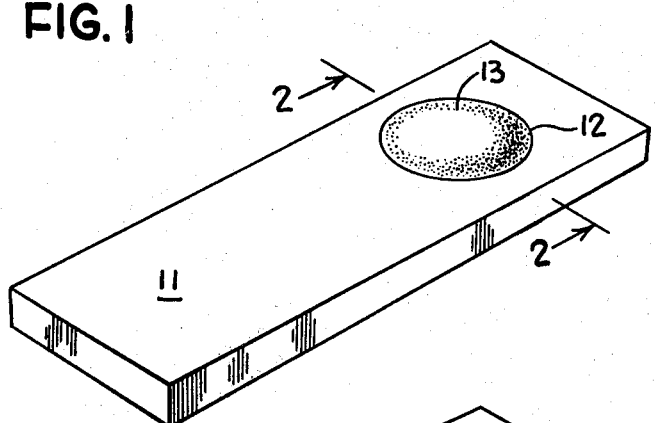
FIG. 2
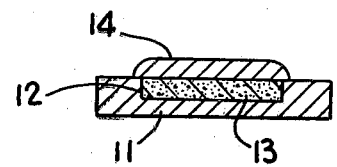
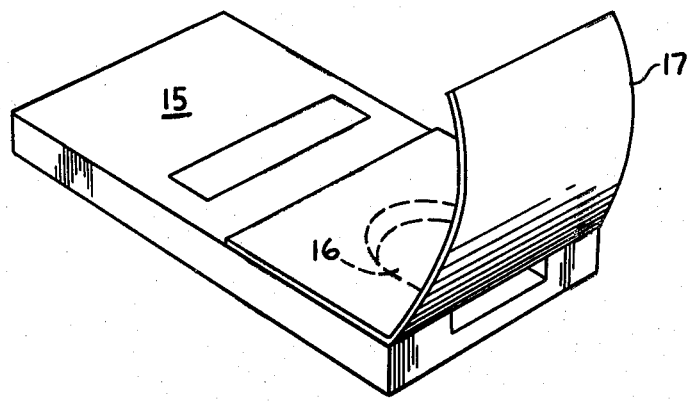
FIG. 3
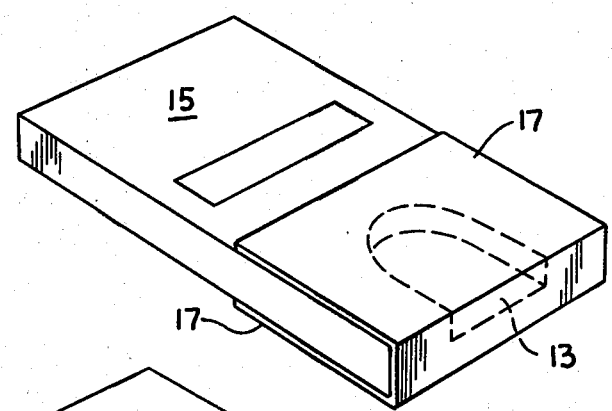
FIG. 4
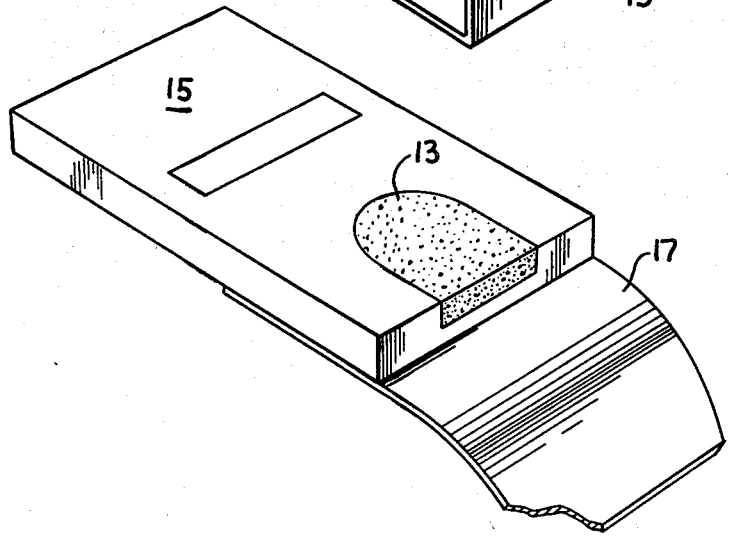
FIG. 5

FIG. 6
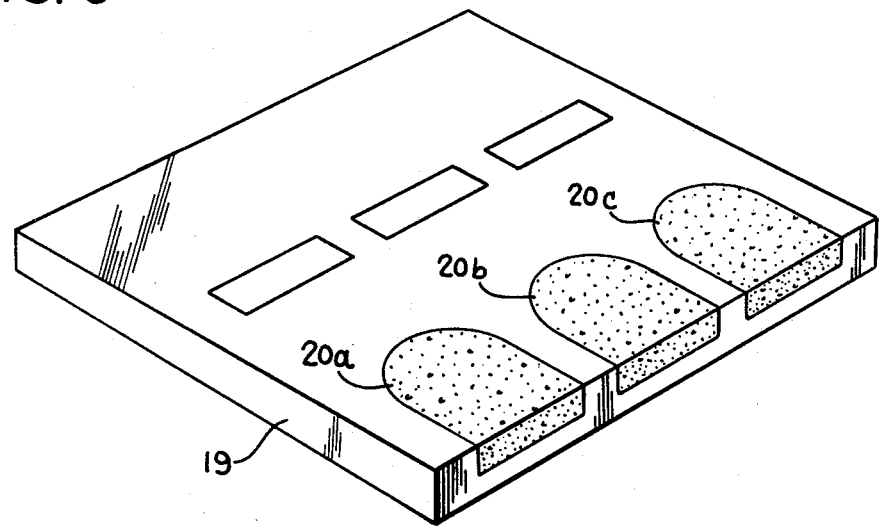
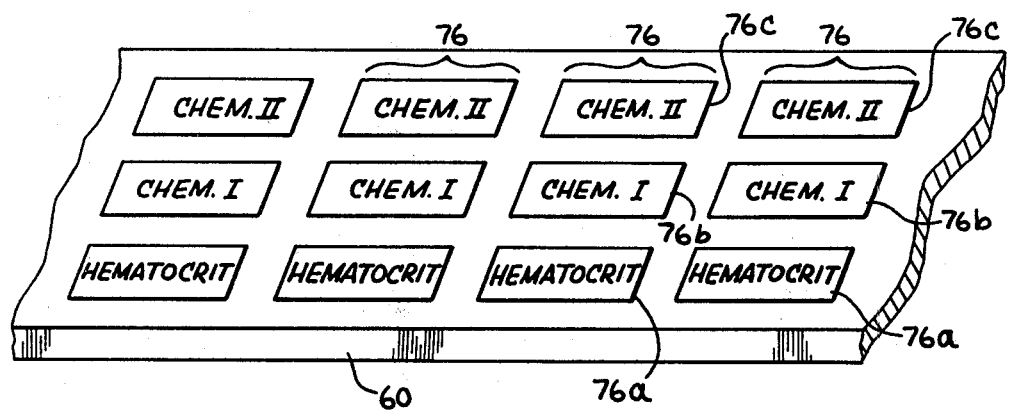
FIG. 10

OUTWARD DIFFUSION OF B-12 FROM AGAROSE GELS INTO WHOLE BLOOD

CORRELATION OF GEL HcT TO CENTRIFUGAL HcT

EFFECT OF IMMERSION TIME ON THE LOSS OF B-12 FROM AGAROSE GELS INTO BLOOD

EFFECT OF HcT ON GEL ALBUMIN ASSAY

WHOLE BLOOD ANALYSES IN POROUS MEDIA

FIELD OF THE INVENTION

The invention relates to method and apparatus for analyzing whole blood samples and more particularly for determining hematocrit and hematocrit effects in whole blood samples.

BACKGROUND OF THE INVENTION

It is known in the prior art to perform assays of whole blood using gel media. In the Martin J. Lee et al, U.S. Pat. No. 3,990,849, assigned to a common assignee, a technique is shown for separating the solid and liquid phases of whole blood using a gel medium. Assays of the analytes within the liquid phase of plasma are then performed after such separation and within the gel medium.

A more recent U.S. patent application to Martin J. Lee, Ser. No. 922,611, filed July 7, 1978, also assigned to a common assignee, teaches how to obtain precise aliquots of plasma, and of analytes or other reagents within the gel medium by controlled diffusion. Such precise aliquots are obtained without the need to measure the sample being tested.

All of this previous work has the objective of performing assays in a quick, simple and cost-effective manner.

A difficulty exists, however, in diffusing precise aliquots of blood plasma from whole blood samples into the gel media by use of the previously-taught methods. Diffusing plasma solutes from whole blood samples into a gel or other porous medium assumes the same rate of plasma solute diffusion for each blood sample such that a constant aliquot is obtained within such medium for all blood samples. Such is not always the case. The hematocrit of the whole blood sample affects the rate of diffusion of the plasma solutes entering into a gel medium. Precisely controlling the time of diffusion, therefore, does not produce a constant aliquot of plasma within the gel media for all samples. A precise aliquot of plasma within the gel medium is needed, however, in order that quantitative analyses can be performed on the analytes within the blood sample.

The subject invention teaches a means of determining the hematocrit in whole blood by diffusion methods, and the effects of hematocrit on whole blood assays. Also, the invention teaches the correction for hematocrit effects when using diffusion apparatus methods to perform assays.

The invention further teaches how an analyte can be directly determined from the plasma of a whole blood sample diffused into a gel or other porous medium by observing two color changes within the porous medium: (1) the color change due to an outward diffusion of dye from the medium as a function of the hematocrit of the blood sample, and (2) the color change due to reaction of an analyte in the plasma of the sample with a reagent disposed in the porous medium.

SUMMARY OF THE INVENTION

The present invention pertains to a method and apparatus for analyzing whole blood samples without need for prior separation of the samples into cellular and plasma constituents.

It is contemplated that a gel or other porous medium be used to obtain a precise aliquot of plasma from a whole blood sample by diffusion techniques. The whole blood sample is placed on a prescribed surface area of the medium, and the plasma is allowed to diffuse into the medium for a controlled period of time. If the whole blood sample were only comprised of plasma, a constant aliquot of the plasma would be obtained within the medium at the end of this controlled time period as taught by U. S. Ser. No. 922,611.

However, due to red blood cells present in whole blood samples, diffusion of the plasma is somewhat inhibited. As some of the red cells cover a portion of the prescribed medium surface area, the surface area is effectively reduced, the mean diffusion path for solute molecules to reach the gel surface is increased and the rate of plasma solute diffusion is reduced. The effect on the diffusion rate of the plasma components of different whole blood samples will vary, because the fraction comprising blood cells will vary between different samples. As such, constant aliquots of plasma cannot be obtained, because of variations in the hematocrit of such samples.

The invention teaches the use of a correction factor for the hematocrit variation to precisely determine the plasma aliquot diffused into a gel medium. This correction factor can be obtained in several ways (a) the hematocrit may be first determined in a separate gel and a correction factor then calculated for assays performed in other gel media using different portions of the whole blood sample, or (b) the reaction of an analyte in the plasma of the whole blood with a reagent in the gel medium may be determined directly by measuring two color changes: (1) that resulting from the analyte-reagent reaction; and (2) that resulting from the loss of dye from the medium as a function of hematocrit in the whole blood sample, as will be described in more detail, hereafter.

In method (a), the hemaocrit effect is determined by incorporating an inert indicator within a separate porous medium not containing any other reagents. This inert indicator can be a colored molecule such as vitamin B-12 (cyanocobalamin), which will not significantly react with the whole blood sample. It is known that substances within the porous medium diffuse outwardly therefrom, as the plasma diffuses into the medium from the whole blood sample. The blood cells will block diffusion of the escaping inert dye in a similar manner as the plasma solutes are blocked from entering the medium. Experiments have shown that the diffusion of the dye from the gel or other porous medium is proportional to the rate at which the plasma solutes diffuse into the gel. Furthermore, the diffusion of the dye has been found to be inversely proportional to the hematocrit of the blood sample. From these experiments, a correction factor can be determined based upon the loss of dye from the medium. This correction factor allows calculation of the concentration of any particular analyte present in the plasma. Further, it has been shown that the hematocrit determination using diffusion techniques is comparable to the hematocrit determined from standard centrifugation (separation) techniques.

It is very important that the dye contained within the gel or other porous media be non-reactive with any part of the whole blood sample, i.e., either plasma solutes or blood cells. This is so because any reaction, clumping, or coagulation within the blood sample may influence the diffusion rate, and thus, effect the correction factor.

In method (b), optical measurements are conducted concurrently for determining the reaction product of an analyte within the medium and the loss of dye from the same medium. This necessitates that the color change due to the loss of dye from the medium in no way interferes with the color change due to the analyte reaction.

In this procedure, a direct assay for the analyte is made by measuring both color changes within the same medium. The dye color and the reaction color should not interfere with each other over their respective color change rate.

The apparatus of the invention can be briefly summarized as featuring a porous medium having a prescribed surface area upon which a quantity of whole blood is placed. An inert substance is disposed within the medium for out-diffusion from the medium when the whole blood sample is placed on the prescribed surface area for diffusion into the medium. The inert substance is inert with respect to the whole blood sample, i.e., both the plasma solutes or the blood cell portions.

The method of the invention can be briefly summarized as comprising the steps of:

(a) contacting a surface of a medium containing an inert substance with a whole blood sample;

(b) diffusing at least a portion of the plasma solutes of the whole blood sample into the medium, and (c) diffusing at least a portion of the inert substance from within the medium across the surface contacted by said whole blood. The amount of diffusion of the inert substance from the medium is a measure of the value of hematocrit in the whole blood sample.

It is an object of this invention to provide an improved method and apparatus for assaying whole blood without prior separation of the whole blood into its constituents.

It is another object of this invention to provide a method and apparatus for performing whole blood assays using diffusion techniques.

It is a further object of this invention to provide a method and apparatus for assaying of whole blood samples using gel diffusion techniques.

It is yet another object of this invention to provide a method and apparatus for determining hematocrit and correcting for its effects upon the obtaining of precise assays of whole blood samples.

It is still a further object of this invention to provide a hematocrit correction factor for whole blood assays involving diffusion techniques for obtaining aliquots of the blood plasma within porous media.

BRIEF DESCRIPTION OF THE DRAWINGS

These and other objects of this invention will become more apparent and will be better understood with respect to the following detailed description taken in conjunction with the accompanying drawings, in which:

FIG. 1 is a perspective view of one embodiment of the present invention;

FIG. 2 is a cross-sectional view of FIG. 1 taken along line 2—2 with a drop of a whole blood sample in place.

FIG. 3 is a perspective view of another embodiment of the present invention with a flexible cover over a portion of the to-be-filled cavity.

FIG. 4 is a perspective view as in FIG. 3 with a transparent tape closing off the entire cavity having been filled with a porous medium containing an inert substance.

FIG. 5 is a perspective view as in FIGS. 3 and 4 with the transparent tape in the process of being removed.

FIG. 6 is a perspective view of yet another embodiment of the present invention.

FIG. 10 is a perspective view of an example of a contiuous tape construction for the automated systems shown in FIGS. 8 and 9.

DETAILED DESCRIPTION OF THE EMBODIMENTS OF THE INVENTION

Attention is now directed to the drawings for a consideration of various structural embodiments of the invention. In FIGS. 1 and 2, a flat rectangularly shaped support 11 is shown, which defines a well 12 filled with a gel or other porous medium 13, e.g., agarose containing an inert substance, e.g., vitamin B-12. The support 11 may be constructed of plastic or glass. While dimensional characteristics are not extremely important, it is contemplated that the well 12 will be of from 0.1 to 2 mm in thickness and of from 5 to 20 mm in diameter. The embodiment disclosed in FIGS. 1 and 2, employs a well 12 of 1 mm in depth and 8 mm in diameter. The well is generally centered on the support 11 at a location wherein the gel will intersect the light beam of a suitable photometer or spectrophotometer. The gel should preferably fill well 12 to the surface whereby good contact is made with the supply of the whole blood sample. For instance, when a drop of whole blood sample 14 is utilized, the drop must overlap the portion of the support surrounding the well. The necessity of filling the well to its fullest extent with the gel is even more important when the application of the sample is by way of a supplemental carrier. For example, a whole blood sample may be incorporated in a capillary web. Such a web is then brought into touching confrontation with the surface of the gel. The plasma portion of the sample diffuses into the gel directly from the whole blood sample loaded capillary web. After a pre-selected period of time, the web may be removed from the surface gel. The plasma penetrating into a portion of the gel is simultaneously diffused into the gel as the inert substance diffuses from the gel into the whole blood sample. At the end of a given time period, the inert substance will have diffused from the gel a given amount which is inversely proportional to the hematocrit (HcT) in the whole blood sample.

Figure 11:
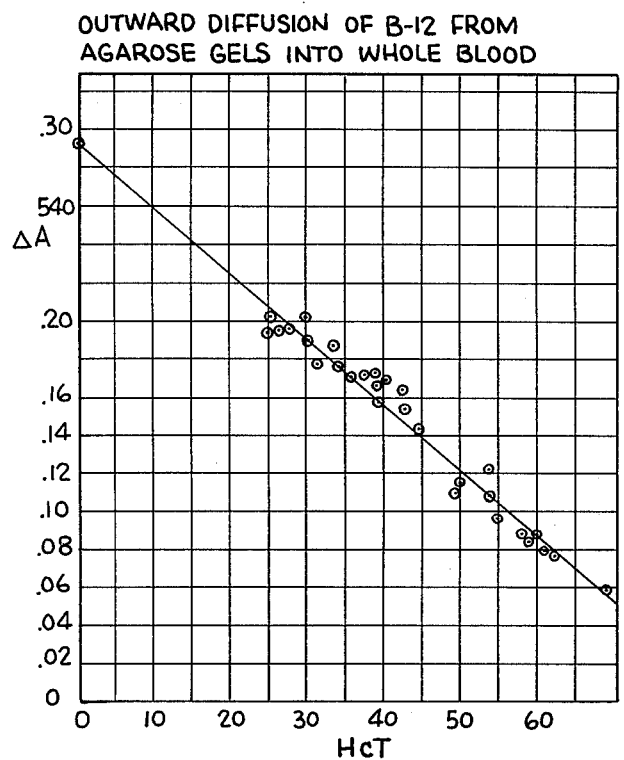
FIG. 11 is a graph showing the diffusion of vitamin B-12 from agarose into whole blood as a function of hematocrit (HcT).
Figure 12:
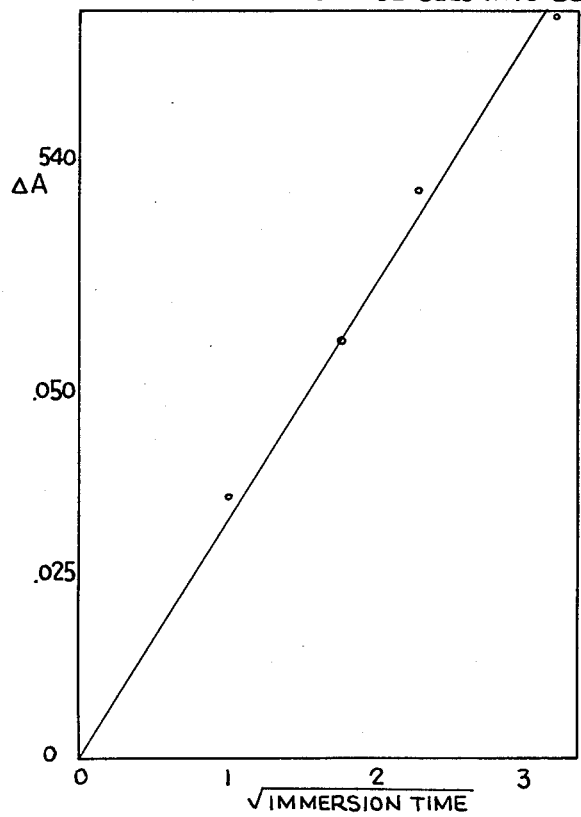
FIG. 12 is a graph showing that vitamin B-12 will diffuse from agarose as a square root function of time as predicted by the diffusion laws.

Support for this proposition is shown by reference to FIGS. 11 and 12, respectively. FIG. 12 shows that diffusion of the inert substance, (in this instance vitamin B-12 (cyanocobalamin)) from the agarose gel medium into a whole blood sample follows Einstein's Law of Brownian Motion, reference: *Introduction to Colloid*

*Chemistry*, K. J. Mysels, Interscience (1959) N.Y. Note that diffusion as measured by decrease in absorption is a similar function of the square root of time.

FIG. 11 illustrates that the outward diffusion of the inert substance (vitamin B-12) from the gel medium is a linear function of the amount of hematocrit (HcT) in the whole blood sample.

Attention is now directed to FIGS. 3, 4 and 5. It is here taught that a support has a U-shaped cavity 16 at one surface of the support 15. The broad end of the cavity 16 is open at the end of the support. The arrangement of this embodiment lends itself to large-scale fabrication. This is accomplished by sealing the major open surface of a plurality of like supports with pressure sensitive adhesive tape 17, but with the end portion of the cavity in an open condition, through which the gel 13 may be loaded into the cavity. The gel is permitted to harden. Thereafter the remaining loose portion of the adhesive tape 17 is wrapped around the end of the support to seal the reamining portion of the cavity 16. In this embodiment, the device may be used as a dip stick for immersion in the sample for a predetermined time. The tape 17 is removed prior to use. The dip stick is then immersed in the liquid whole blood sample for a predetermined period of time which is sufficient to permit plasma solutes of the whole blood sample to diffuse into the porous medium and, simultaneously therewith, the inert substance to diffuse from the medium into the blood sample.

FIG. 6 is similar to the embodiments shown in the aforementioned embodiment of FIGS. 3, 4 and 5. A plurality of cavities 20a, 20b, and 20c are disclosed, however, so that a plurality of tests or assays may be performed on a single support 19 in addition to determining the hematocrit effect for the whole blood sample. The whole blood is placed in overlapping fashion over all three respective cavities 20a, 20b, and 20c. Cavity 20a may contain a gel with the inert dye for hematocrit determination, while the cavities 20b and 20c may contain gels with reagents for reaction with particular plasma analytes.

In the foregoing, the assembly has been a substrate having a well therein, or at least some sort of depression. Within the purview of the instant invention, it is indeed contemplated that a dip stick also be constructed from a specially prepared roll of tape. Accordingly, attention is directed to FIG. 7 for such an arrangement. Initially, an elongated transparent tape is given a coating of a gel on at least one surface. The gel is permitted to set up or harden thereon, although a certain degree of flexibility may be desirable for handling purposes. The gel is as before, i.e., charged with the inert substance for use in determining the hematocrit in the whole blood sample.

Figure 7:
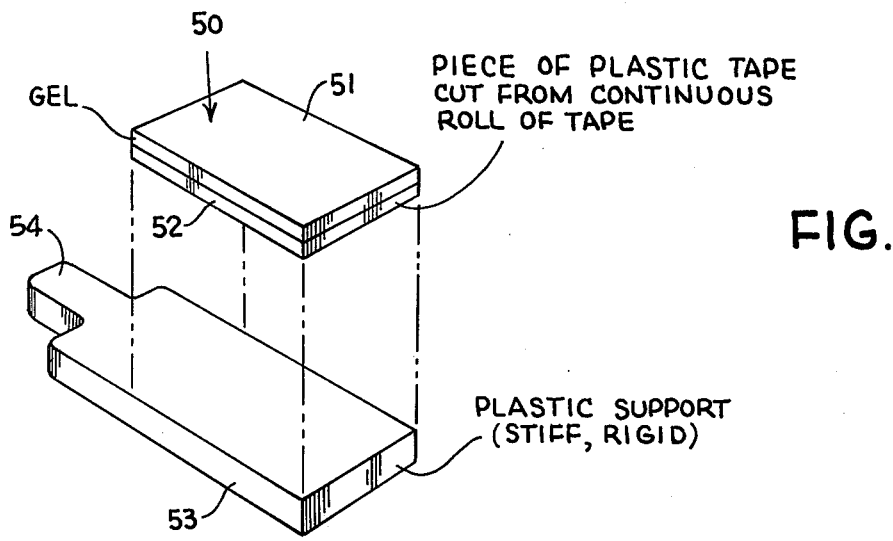
FIG. 7 is another embodiment showing a perspective view of a dip stick configuration of the inventive apparatus.

The resultant tape is cut into suitable composite lengths 50 as shown in exploded FIG. 7. The gel 51 is facing upwardly, while the tape substrate 52 is underneath. The substrate 52 has an amount of adhesive coated on its underside. The composite is secured to a fairly rigid plastic support 53 which may be relatively longer than the length 50. The extended portion may comprise a handle 54, by means of which the dip stick may be inserted in a quantity of a liquid whole blood sample as heretofore mentioned. It is further contemplated that the tape shown in FIG. 7, may be used in a form whereby portions are not cut, but the entire roll is used in an automated system. Accordingly, attention is directed to FIG. 10. FIG. 10 shows a tape 60 having a series of groups of gels having the form of "chips" 76. Each group of "chips" (gels) comprise a chip 76a containing an inert dye for the hematocrit assay, and two other chips 76b and 76c, respectively, containing reagents for two other assays of analytes in the blood plasma. The tape 60 is used in the automated system shown in FIG. 8. Reading from right to left, note that a gel tape 60 is unwound from a feed reel 61 and travels horizontally along a path delineated by arrows. The tape 60 passes a sample application station 62, whereat discrete whole blood samples are dropped. A vibratory agitator 71 is disposed adjacent the tape 60 at the application station 62 to mix the sample and prevent sedimentation of red cells in the whole blood sample, while the plasma solutes are diffusing into the gels. Determination of the hematocrit effect may not be precise if sedimentation of the red cells is allowed to take place during diffusion of the plasma solutes into the gels. The path and traversing speed of the tape is such, that sufficient diffusion will take place in the gel. At station 63, the remaining whole blood sample is briefly rinsed away by suitable means well known in the art. At the next station 64, the tape is incubated to permit further diffusion for gels 76b and 76c, such that their reagents may react with the analytes in the plasma as described in U.S. application Ser. No. 922,611. Thereafter, the tape 60 is delivered to a reader station 65, at which point the reactant areas are optically read in a conventional manner. The tape may then be rewound by a take-up reel 66. Reader 65 comprises two sections 65a and 65b, respectively. Section 65a optically measures the color change in the hematocrit gel 76a. Section 65b optically measures the color changes in gels 76b and 76c, to determine the analytes present. The optical measurement from section 65a is fed to a memory or other device 74 to obtain a hematocrit correction factor. The correction factor is fed back to reader 65b to obtain a corrected value for the analytes in gels 76b and 76c. The corrected analyte values are then recorded by a recorder 75 or other suitable output device. The gel 76a can be read after initial diffusion time for a color change due to the loss of the dye from the gel medium, but for purposes of automation may be read along with gels 76b and 76c at reader station 65.

In the foregoing embodiment, the tape substrate may be any one of several well known transparent plastic materials, such as polyethylene terphthalate (mylar), polyethylene, polypropylene, methyl-methacrylate (lucite), etc.

Figure 8:
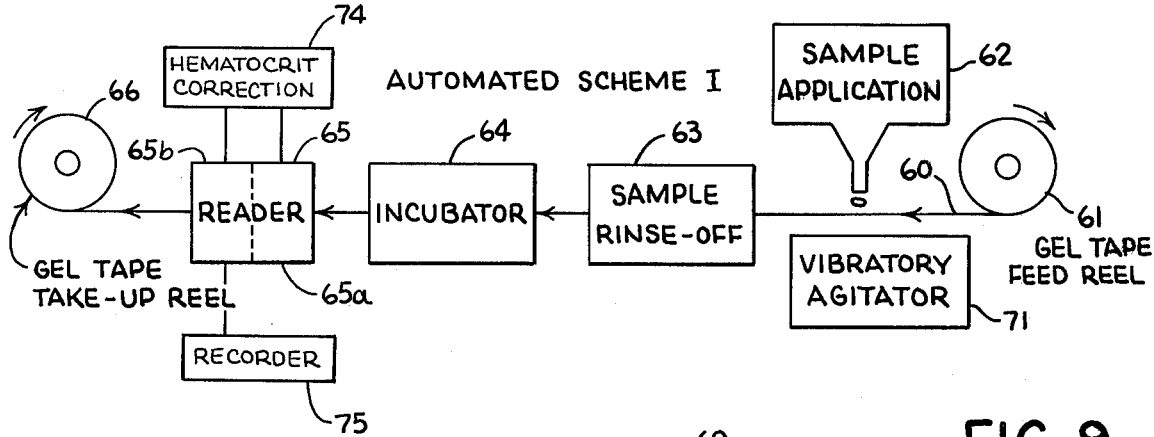
FIG. 8 is another embodiment showing an automated system in a diagrammatic manner.
Figure 9:
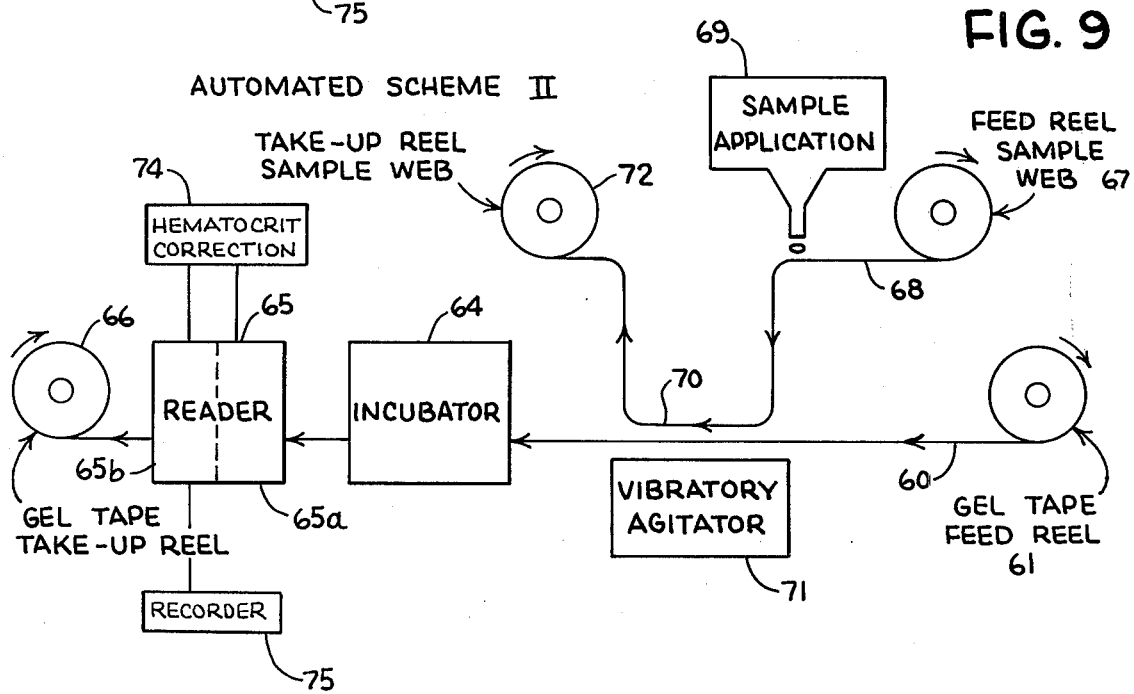
FIG. 9 is yet another embodiment showing an automated system also in a diagrammatic manner.

Attention is now directed to FIG. 9 for a review of still another automated system shown in a schematic manner. Again, a gel tape 60 is positioned on a reel 61. In this embodiment, the sample drop is not applied directly to gel tape 60. Rather, a secondary supply reel 67 is employed which carries an aqueous permeable web 68. The web 68 may be comprised of cellulose, cellulose acetate, nylon, or other wettable and solute permeable materials. The web 68 is discharged from reel 67 along a path that traverses a sample application station 69. The sample application station 69, delivers a sample drop to web 68. The sample drop penetrates the web 68 by diffusion or capillary action, thus allowing the sample to wet the gel tape 60 through the underside of web 68 as it comes into touching contact at position 70. A sufficient period of time is needed to cause diffusion of the plasma solutes of the sample from tape 68 into the gel tape 60. After the web 68 and the tape 60 part, the web 68 is wound on takeup reel 72. A vibratory agitator 71 may be positioned adjacent position to 70 in order to prevent sedimentation of red cells, i.e., avoid the hematocrit effect as aforementioned. After diffusion of the plasma solutes into the gels, the tape 60 continues travelling along its path (delineated by arrows) to an incubator 64, as previously shown in FIG. 8. Thereafter, the tape is advanced to the measuring station 65 for analysis purposes. Reader 65 comprises two sections 65a and 65b, respectively. Section 65a optically measures the color change in the hematocrit gel 76a. Section 65b optically measures the color changes in gels 76b and 76c to determine the analytes present. The optical measurement from section 65a is fed to a memory or other device 74 to obtain a hematocrit correction factor. The correction factor is fed back to reader 65b to obtain a corrected value for the analytes in gels 76b and 76c. The corrected analyte values are then recorded by a recorder 75 or other suitable output device. Finally, the tape 60 is wound upon the tape-up reel 66.

It will be appreciated that the present invention lends itself to the concept of perfoming various clinical chemical assays with whole blood samples. The tape 60 of FIG. 10 may be made from mylar, polystyrene, or other suitable transparent material.

The aforementioned chips 76 of FIG. 10 are adhesively positioned in space-apart relationship on tape 60. The first row of chips 76a is used to determine the hematocrit effect of the whole blood sample so that the analyte assays of the other gels 76b and 76c can be corrected. The second row of chips 76b may be all devoted, for example, to an albumin assay. The third row of chips 76c may all be used for a glucose assay for instance. Other chips 76d, 76e, etc. (not shown) may also be included on tape 60 to perform still more assays such as LDH, etc.

The measuring station 65 is adapted to analyze the reaction results obtained in corresponding chips in correlated fashion with respect to each whole blood sample.

In the foregoing system, a series of discrete chips 76 are shown. It is also contemplated that the chips may be non-discontinuous so that parallel elongated strips may be employed, i.e., one for each of the selected assay as desired.

Linearity in a chemical assay system is an important criterion of reliable performance. Linearity implies a first order kinetic reaction so that concentration of test substances may be easily assayed. It is well known that in order to obtain linearity, it is necessary to have excess reagent in the medium. This is accomplished in our gel system by carrying out the assay in a two-step process.

Also, certain analytes may be determined by measuring the rate of reaction of enzymes contained within the gel.

The operation of the aforementioned systems for assaying analytes will be described in the following discussion. Contact is made between a well-defined surface of the gel and the sample for a brief period of time, i.e., of the order of 10 to 60 seconds. The sample is then removed. This will allow diffusion of the sample analyte into the surface region of the gel. It should prove evident that conditions may easily be selected, whereby the depth of penetration of the analyte molecules will be small relative to the thickness of the gel. This procedure will create a "reservoir" of analyte near the outwardly facing portion of the gel.

To be most effective, a further diffusion of the analyte into the gel is required after removal of the sample liquid from contact with the gel surface. This will permit redistribution of the plasma solutes of the sample throughout the gel. It is submitted that the subsequent diffusion is equivalent to performing the mixing of a known dilution of the sample substance in comparable solution chemistries. The plasma solutes of the sample will now be distributed throughout the gel with equal concentration at all points, and at lower concentration than in the original sample being tested. It will be appreciated that by means of this arrangement of a two-step diffusion process, the usual prior art aliquot procedures and dilution process have been replaced. This method is also useful in obtaining an aliquot and diluting interferants in the sample, thereby lessening their influence on the analysis. Furthermore because of the sample dilution, lower concentrations of reagents are required to completely react with the sample. Such salutary conditions are advantageous for the establishment of first order reaction kinetics and calibration curves that are linear with analyte concentration. However, as previously stated, the time dependency of the reaction is not linear due to the fact that the distance of diffusion is a square root function of time. Thus, errors in measuring the time during which the gel is exposed to a liquid sample produces smaller analytical errors that are proportional only to the square root of time.

As used herein, the term gel relates to a material in which a polymeric substance forms a matrix having a given three-dimensional shape. The mechanism of such behavior is only partially understood, but such materials contain relatively large quantities of solvent which is an integral part of the gel material. The choice of a matrix material is, of course, variable and dependent on intended use. Desirable matrix materials for aqueous gel media can include hydrophilic materials including both naturally occurring substances like gelatin, gelatin derivatives, hydrophilic cellulose derivatives, polysaccharides such as dextran, gum arabic, agarose and the like, and also synthetic substances such as water-soluble polyvinyl compounds like poly(vinyl alcohol) and poly(vinyl pyrrolidone), acrylamide polymers, etc.

It is contemplated that any analytical procedure can be adapted to the herein disclosed invention. While the apparatuses and method herein disclosed are particularly suitable for routine whole blood chemistry such as glucose, blood urea, nitrogen, uric acid, albumin, creatinine, bilirubin, phosphate, total protein, amylase, calcium, etc., numerous other analytical tests which are run periodically can be automatically performed in accordance with the precepts of the invention.

While the automatic systems shown in FIGS. 8 and 9 have been discussed with reference to a method wherein hematocrit is determined independently from the blood chemistry assays, it is also possible that automated systems will determine hematocrit and analyte using the same gel medium. In such a system, all the chips 76 will contain an inert dye along with reagents needed for the particular analyte under assay. After the plasma solutes have diffused into the gels from the whole blood sample, and have been further incubated at station 64, the reader station 65 will measure two color changes. These color changes can be read by usual photometric means. The first of the two color changes will relate to the loss of inert substance from the gels as a function of the amount of hematocrit in the whole blood samples as previously illustrated in FIG. 11. This reading may be accomplished within or without the gel medium, since the loss of the inert substance from the medium can be observed in the gel or in the whole blood disposed on the gel. The second of the two color changes pertains to the chemical reaction in the gel between the analyte under assay and its particular reagent. The second color of the analyte reaction will give an indication of the amount of analyte in the blood plasma without the hematocrit correction. The reader station 65 would determine the hematocrit from the first color indication, and automatically correct the value obtained via memory 74 for the concentration of analyte obtained from the second color indication.

In such a method, it would be necessary that the color range for the dye loss should not interfere with the color change produced by the analyte-reagent reaction. Also, it is necessary that the inert dye not react with the reagent in any way which will influence either color reading or the diffusion effects.

Having now discussed the various embodiments of the invention, the discussion will now focus upon how the hematocrit correction is made.

Figure 14:
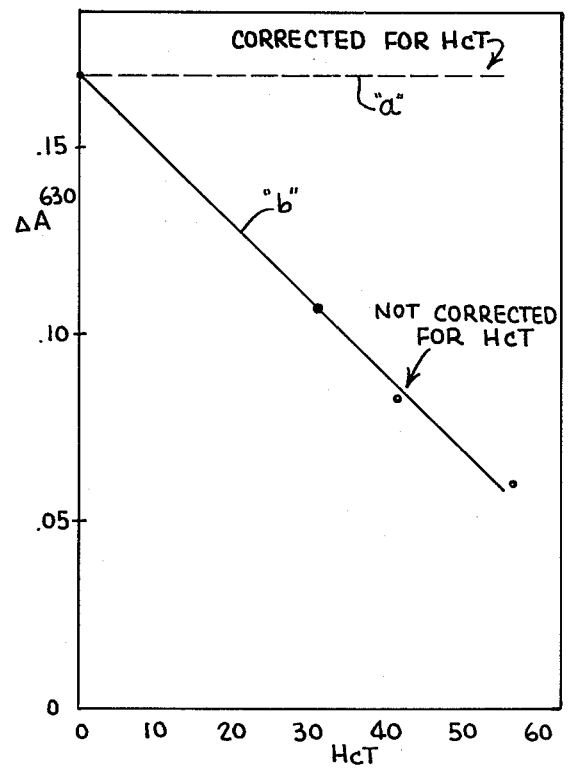
FIG. 14 is a graph of the effect of hematocrit (HcT) on an albumin assay.

Reference is now made to FIG. 14, wherein a typical assay (in this instance—albumin) has been conducted for whole blood samples of varying hematocrit content. Line "a" depicts the true (corrected) albumin content in the whole blood samples, and line "b" illustrates the effect of increasing hematocrit upon the absorbance at 630 nm. As can be seen, the absorbance for the albumin assay will decrease as the amount of hematocrit increases in the blood samples. As aforementioned, it is believed that the blood cells act to block the surface of the gel and restrict diffusion of the plasma solutes of the whole blood sample into the gel. As a result, less plasma solutes and hence, less albumin will finally be disposed within the gel after a given period of time. Therefore, there will be a weaker reaction between the albumin analyte and the reagent due to the hematocrit effect. This weaker reaction will result in the observed decrease change in absorbance.

From data gathered for each analyte under assay, the effects of increasing amounts of hematocrit in the whole blood samples can be determined. This will provide correction factors for adjusting the optical readings to reflect the true values for the amounts of analytes as shown for the albumin assay in FIG. 14.

Figure 13:
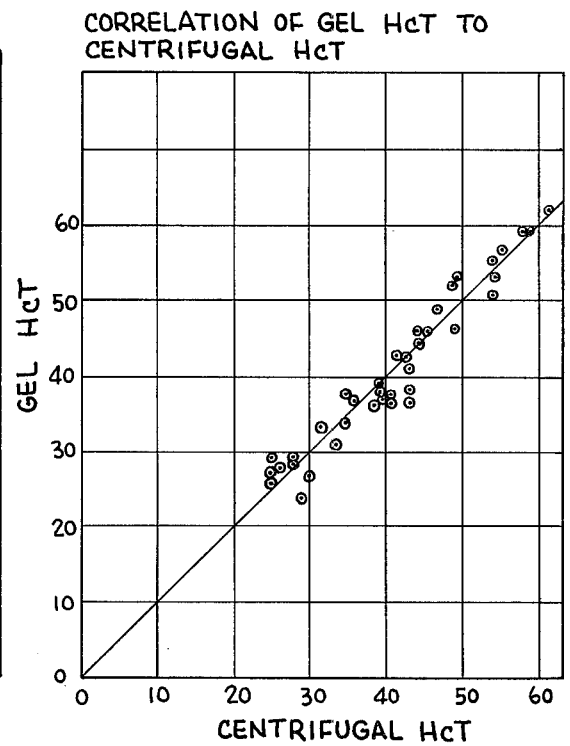
FIG. 13 is a graph showing the correlation between the hematocrit (HcT) determined by diffusion and by standard centrifugation techniques.

FIG. 13 depicts a graph correlating the hematocrit determinations for various blood samples as performed by the diffusion methods of the invention, compared with the hematocrit determinations for these samples made by standard centrifugation techniques. As can be observed from the graph line, the amounts of hematocrit as determined by the diffusion techniques of the invention are equivalent to the determinations derived from the standard centrifugal procedure.

The following examples will be found useful in further understanding the FIGS. 11-14:

EXAMPLE I - PREPARATION OF VITAMIN B-12 IN AGAROSE GEL

In a 25 ml Erlenmeyer flask, place 0.1 g of agarose and 9.00 ml of PBS (see below). Place in a boiling water bath for 5 minutes in order to dissolve the agarose. Allow to cool to 50° C. and add 1.0 ml of 1.0% vitamin B-12 (in PBS). The gel sticks are then made by delivering 2-3 drops of this warm solution into the wells and overlaying them with a plastic cover. If the gels are not to be used immediately, they may be stored at room temperature in a humidified container. The red color of the gels was found to be very stable upon storage at room temperature or in the refrigerator for several months.

PBS, phosphate buffered saline, contains the following materials per liter: 80 ml of 0.1 M $Na_2HPO_4$, 20 ml of 0.1 M $KH_2PO_4$, 8.5 g of NaCl and 0.2 g of $NaN_3$, pH=7.3.

EXAMPLE II - DETERMINATION OF THE GEL HEMATOCRIT BY VITAMIN B-12 OUTWARD DIFFUSION FROM THE GEL MEDIUM

The initial absorbance at 540 nm is read for each gel stick with a blank agarose gel as reference. The gel sticks are then immersed in a b 1.5 ml sample of whole blood of known centrifugal hematocrit (HcT). The immersion process is typically 10 minutes in length. The gel sticks are removed from the blood and quickly rinsed free of blood by dipping into two beakers of clean PBS. Following this, absorbance at 540 nm is again determined. The absorbance change at 540 nm, $\Delta A = A$ initial $- A$ final is then determined.

Experimental data were plotted with $\Delta A$ 540 as ordinate versus centrifugal hematocrit (HcT) as bascissa. In FIG. 11, the results of 49 whole blood samples are shown. Each centrifugal hematocrit (HcT) was the mean of a duplicate set determined by the 7-minute micro method.

EXAMPLE III—PREPARATION OF GELS FOR THE ALBUMIN ASSAY

In a 25 ml Erlenmeyer flask, place 150 mg of agarose, add 7.0 m of succinate buffer (defined below) pH 4.4. Dissolve the agarose by immersion of the flask into a boiling water bath for approximately 5 minutes. Then add 3.0 ml of 1.5 mM Bromcresol Green (BCG) solution, mix and stop heating. The gel sticks are prepared as described under B-12/agarose gels.

Succinate Buffer: In 800 ml of distilled water, dissolve 8.85 g of succinic acid (75 m moles), bring up to pH 4.2 by addition of NaOH pellets, then add 5.0 ml of Brij-35, a 30% surfactant solution and 5.36 g of sodium chloride. Dilute to 1 L.

EXAMPLE IV—DETERMINATION FOR THE GEL ALBUMIN ASSAY

The initial absorbance of each gel dip stick is read at 630 nm. Place 1 drop of whole blood, plasma or serum on the surface of the gel for exactly 30 seconds, then quickly rinse off the sample in two washes of clean succinate buffer. Read the final absorbance at 630 nm after 20 minutes. A plot of 66 $A630$ versus hematocrit (HcT) at fixed plasma albumin concentration is shown in FIG. 14 which illustrates the hematocrit effect.

In general, as used herein, the term "inert substance" refers to a material which is soluble in a solvent; and inert with respect to the cell or particulate fraction and substances dissolved in the solvent. Specifically, it must not bind to, or react with, dissolved molecules, cells, or particulate matter. It must not transport either passively or actively into the interior of cells or particles. This interior space will, therefore, remain an excluded volume. Also, this material must have a low enough effective molecular diameter with respect to the average pore size of the gel media, so that it is diffusible within that media, and across the solvent-gel boundary.

The use of various inert dyes has been contemplated for the hematocrit determination. Vitamin B-12 (cyanocobalamin) is one of these dyes and is a good choice because it is easily obtainable, in pure form, exhibits very little binding with plasma proteins, (human plasma contains roughly 100 ng/ml of vitamin B-12 binding proteins called transcobalamins, reference: Allen, R. H. and Majerus, P. W.: Journal of Biological Chemistry 23(10); 7695, (1972), and has a spectral range that is easily observable by photometric methods. Inert dyes which will work in the inventive method for determining hematocrit will particularly have the following requirements:

(a) they must be water soluble; (b) they must have minimal electrical charge, and (c) where optically measured, they must have a large molar absorptivity in the visible region, preferably at a wavelength which can be discriminated.

Vitamin B-12 fits the above requirement. It is a large molecule (molecular weight of 1355) that has only one negative charge in the nucleotide. The $+3$ charge on the cobalt is highly delocalized by hexaligation. The absence of highly charged groups is needed so that the molecule will not bind to the albumin and other proteins. Also, being a large molecule is helpful in discouraging binding by virtue of steric hindrance effects. By electrically neutral, we mean to minimize ionic groups such as: $CO_2-$; $NH_3+$; $NR_2H+$: $NRH_2+$; $SO_3-$; etc. which are commonly used to produce water solubility in polyaromatic dyes.

The solubility of the vitamin B-12 molecule is provided via polyhydroxylation by a number of "OH" (hydroxyl) groups and "—O—" (ether linkages). The

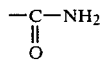

groups are also polar. However, the solubility of the molecule is mainly derived from the nucleotide.

It is further contemplated in keeping with the teachings of the invention, that the aforementioned diffusion technique may be used in a test for concentration of particulates in a solution other than blood. Such a solution may be, for example, another biological solution or a solution of manufactured substances, etc.

Having described our invention, what is desired to be protected by Letters Patent is presented by the following appended claims.

What is claimed is:

1. A method of determining the concentration of particulate in a solution, comprising the steps of:
   (a) contacting a surface of a medium containing an inert substance with a solution containing particulate, said inert substance being inert with respect to said solution and said particulate;
   (b) diffusing at least a portion of said solution across said surface into said medium;
   (c) diffusing at least a portion of said inert substance from within said medium across the surface contacted by said solution, the diffusion of said inert substance from the medium being indicative of the amount of particulate in said solution; and
   (d) determining the concentration of said particulate in said solution as a function of said inert substance diffusing from said medium.

2. A method of determining hematocrit in a whole blood sample, comprising the steps of:
   (a) contacting a surface of a porous medium containing a water soluble inert substance with a whole blood sample, said inert substance being inert with respect to said whole blood sample;
   (b) diffusing for a period of time at least a portion of plasma solutes of said whole blood sample across said surface into said medium;
   (c) cross-diffusing for a corresponding period of time at least a portion of said inert substance from within said medium across the surface contacted by said whole blood, and
   (d) determining the concentration of said inert substance diffused from within said medium as indicative of the hematocrit of said whole blood sample.

3. The apparatus of claim 2, wherein said inert substance is a colored indicator substance.

4. The apparatus of claim 2, wherein said inert substance is polyhydroxylated.

5. The apparatus of claim 2, wherein said inert substance is a glycoside.

6. The apparatus of claim 2, wherein said inert substance is vitamin B-12 (cyanocobalamin).

7. The method of claim 2, comprising the further step of limiting said diffusing steps (b) and (c) to a controlled period of time.

8. The method of claim 2, further comprising the step of:
   (e) measuring the amount of inert substance remaining in said medium after diffusion thereof, as an indication of the hematocrit of said whole blood sample.

9. The method of claim 2, further comprising the step of:
   (e) washing said surface of said medium to remove any portion of said whole blood sample remaining on said surface after diffusion step (b).

10. The method of claim 2, wherein said medium is transparent and said inert substance has a color, the method comprising the further step of:
    (d) measuring said hematocrit of said whole blood sample by detecting the depth of color of said inert substance in said medium.

11. The method of claim 2, wherein said medium contains an enzyme for reaction with an analyte of said whole blood sample, the method comprising the further step of:
    (d) measuring the rate of reaction of the enzyme.

12. The method of claim 2, wherein the contacting step (a) includes agitating said whole blood sample upon said surface of said medium.

13. The method of claim 2, wherein the diffusing step (b) comprises the further steps of:
    (f) supporting said whole blood sample on a carrier; and
    (g) contacting said carrier to said medium to effect diffusion of said plasma solutes of said whole blood sample into said medium.

14. The method of claim 13, wherein said carrier is a porous medium, and the supporting step (f) includes impregnating said porous medium with said whole blood sample.

15. The method of claim 2, wherein the contacting step (a) includes dispensing said whole blood sample to overlap a prescribed surface area of said medium.

16. The method of claim 15, comprising the further step of defining said prescribed surface area in planar fashion.

17. The apparatus of claim 2, wherein said porous medium is a gel.

18. The apparatus of claim 17, wherein said gel is a hydrocolloid.

19. The apparatus of claim 17, wherein the gel is transparent.

20. The apparatus of claim 17, wherein said gel is selected from a group of materials consisting of: gelatin, gelatin derivatives, hydrophilic cellulose derivatives, polysaccharides, gum arabic, agarose, water-soluble polyvinyl compounds, and acrylamide polymers.

21. The method of claim 2, further comprising the steps of:
  (e) supporting a plurality of porous media on a unitary support;
  (f) contacting each of said plurality of porous media with a whole blood sample, one sample for each of said porous media; and
  (g) determining the concentration of an inert substance diffusing from each of said porous media as indicative of the hematocrit of the respective whole blood sample in contact therewith.

22. The method of claim 21, wherein the medium comprises a reagent for reaction with an analyte in said plasma solutes, and wherein the method further comprises the step of:
  (e) measuring a reaction of said reagent with said analyte.

23. The method of claim 22, further comprising the step of:
  (f) correcting the measuring step (e) by a factor dependent upon the hematocrit of said whole blood sample.

24. The method of claim 22, wherein diffusion of said inert substance provides a first color indication and said reaction of said reagent with said analyte provides a second color indication, said first and second color indications, respectively, being indicative of the hematocrit of said whole blood sample and the amount of analyte in said whole blood sample, the method comprising the further step of:
  (f) determining from said first and second color indications the concentration of said analyte in said blood sample.

25. An apparatus for determining hematocrit of a whole blood sample, said apparatus comprising:
  a gel mass having an exposed prescribed surface area adapted to receive a whole blood sample, whereby contact of said prescribed surface area by said whole blood sample for a given period of time will diffuse an aliquot of plasma solutes from said whole blood sample into said gel mass;
  a water soluble substance contained within said gel mass, said substance being inert with respect to any part of said whole blood sample and diffusable across said prescribed surface area when said gel mass is contacted to said whole blood sample, the quantity of said inert substance diffused from said gel mass being indicative of the hematocrit of said whole blood sample;
  a support for carrying said gel mass and defining said prescribed surface area;
  a reagent disposed within said gel mass for forming a detectable color-reaction product with at least one constituent of said whole blood sample, the presence of said inert substance within said gel mass in no way interfering with or affecting the detection of said color-reaction product; and
  means for independently measuring the said color-reaction product and, also, the amount of said inert substance in either said whole blood sample or said gel mass after said diffusion.

26. The apparatus of claim 25, wherein said support comprises a rigid substrate having said gel mass disposed on one end thereof and a handle disposed on a distal end thereof, and adhesive means for binding said gel mass to said one end of said substrate, said one end of said substrate being immersible in said whole blood sample in dip stick fashion.

27. The apparatus of claim 25, wherein said support comprises an elongated substrate surface defining a well at one end for containing said gel mass.

28. The apparatus of claim 25, wherein said support is an elongated flexible web, and said gel mass comprises at least one strip supported by said web and containing a given quantity of a reagent, said analyte being reactive with said reagent.

29. The apparatus of claim 25, wherein said support is an elongated flexible web and said gel mass comprises at least two separate strips supported by said web, said strips containing given quantities of different reagents, respectively, different respective analytes being reactive with said different reagents.

30. The apparatus of claim 25, further comprising a carrier, means for moving portions of said carrier in contiguous overlapping relationship with said gel mass, said carrier supporting said whole blood sample, whereby at least a portion of plasma solutes of said whole blood sample is caused to diffuse into said gel mass from said carrier.

31. The apparatus of claim 25, wherein said inert substance is a glycoside.

32. The apparatus of claim 25, wherein said inert substance is vitamin B-12 (cyanocobalamin).

33. An automated system for determining the hematocrit of successive whole blood samples comprising: a continuous substrate supporting a plurality of porous media, at least selected ones of said media having exposed prescribed surface areas and containing a known concentration of a water soluble substance inert with respect to any part of said whole blood samples and, also, a given quantity of reagent for forming a color-reaction product with a particular analyte in said whole blood sample, said inert substance being diffusable from said selected media and soluble in said whole blood sample when contacted to said surface areas, a sample dispensing station for dispensing a whole blood sample onto the exposed surface area of each of said selected media for a controlled period of time, a measuring station for independently determining the color-reaction product formed within said selected media and, also, the quantity of said inert substance diffused from each of said selected media, as indicative of the hematocrit of said respective whole blood samples.

34. The automated system of claim 33, wherein said dispensing means includes means for delivering said whole blood sample in dropwise fashion onto said selected porous media.

35. The automated system of claim 33, wherein said dispensing means includes: means for delivering said whole blood samples in successive dropwise fashion onto a movable web and means for advancing said web into contact with said selected porous media supported on said continuous substrate.

36. The automated system of claim 33, wherein a portion of plasma solutes of whole blood sample is diffused into said porous media during said period of time, and further including means for removing undiffused portions of said sample from said porous media after said period of time.

37. The automated system of claim 33, wherein said quantity of reagent in each gel body is in excess of the quantity of said different analyte diffused into said gel body during said period of time.

38. The automated system of claim 33, wherein the dispensing station further comprises agitating means for agitating the whole blood samples.

* * * * *